United States Patent [19]

Nokihara et al.

[11] Patent Number: 5,670,647
[45] Date of Patent: Sep. 23, 1997

[54] METHOD FOR RECOVERING OPTICALLY PURE AMINO ACID DERIVATIVES

[75] Inventors: Kiyoshi Nokihara, Kyoto, Japan; Michael Kiffe, Brunswick, Germany

[73] Assignee: Shimadzu Corporation, Kyoto, Japan

[21] Appl. No.: 609,400

[22] Filed: Mar. 1, 1996

[30] Foreign Application Priority Data

Mar. 2, 1995 [JP] Japan .................... 7-070787

[51] Int. Cl.⁶ .............. C07D 233/40; C07D 233/72; C07K 1/00; C07C 229/00
[52] U.S. Cl. ................ 548/316.1; 530/344; 548/318.5; 562/445
[58] Field of Search ................ 530/344; 562/445; 548/318.5, 316.1

[56] References Cited

PUBLICATIONS

J. Am. Chem. Soc., Louis A. Carpino, 1–Hydroxy–7–azabenzotriazole . . . , pp. 4397–4398, 1993, 115.

Nokihara et al., American Laboratories, Large–scale continuous–flow peptide . . . pp. 41–45, Aug. 1994.

*Primary Examiner*—Floyd D. Higel
*Attorney, Agent, or Firm*—Birch, Stewart, Kolasch & Birch, LLP

[57] ABSTRACT

A method for recovering an optically pure amino acid derivative from a waste liquor collected after a coupling reaction in peptide synthesis, comprising the steps of (a) adding into the waste liquor, in which an uncoupled amino acid derivative or an uncoupled small peptide fragment is contained, a compound selected from the group consisting of 1-hydroxybenzotriazole (HOBt), 1-hydroxy-7-azabenzotriazole (HOAt), 3-hydroxy-4-oxo-3,4-dihydro-1,2,3-benzotriazine (HOObt) and N-hydroxy-5-norbornen-2,3-dicarboxylic acid imide(HONB); (b) concentrating the waste liquor obtained in step (a); (c) treating a residue obtained in step (b) with an acidic buffer solution containing a tertiary amine; and (d) extracting and purifying the uncoupled amino acid derivative or the uncoupled small peptide fragment under acidic conditions.

8 Claims, No Drawings

METHOD FOR RECOVERING OPTICALLY PURE AMINO ACID DERIVATIVES

BACKGROUND OF THE INVENTION

1. Field of the Invention

The present invention relates to a method for recovering an optically pure amino acid derivative from a waste liquor obtained after a coupling reaction in peptide synthesis. More specifically, the present invention relates to a method of recovering the uncoupled amino acid derivative with high optical purity from a waste liquor collected after a coupling reaction in peptide synthesis by suppressing racemization of the amino acid derivative during the recovering process.

2. Discussion of the Related Art

In the present specification, the term "an acyl component" is used as a synonym of "an amino acid derivative" or "a small peptide fragment."

In the preparative, or large scale synthesis of peptide, expensive acyl components are used in large quantities. In the reaction of peptide chain elongation, especially in a solid-phase peptide synthesis, each acyl component is usually used in excess (2 to 10 fold) amounts to gain complete coupling. Thus, in large scale solid-phase peptide syntheses, the recovery and re-use of acyl components are very important for consideration of running costs. In an effort to recover the uncoupled amino acid derivatives from the waste liquor, the present inventors found that a part of the recovered amino acid derivatives did undergo racemization. With regards to degree of racemization, 9-fluorenylmethyloxycarbonyl(Fmoc) -histidine recovered, for example, was found to have a markedly high D-isomer content of 38.8%. Fmoc-tyrosine, Fmoc-aspartic acid, Fmoc-arginine, and Fmoc-phenylalanine were also found to have significantly high D-isomer contents of 2.1%, 1.8%, 1.5% and 1.1%, respectively. Therefore, these recovered amino acid derivatives could not be reused for the synthesis of biologically active peptides [Nokihara et al., American Laboratories, 41–45, August (1994)].

SUMMARY OF THE INVENTION

Accordingly, an object of the present invention is to provide a method for the efficient recovering of uncoupled acyl components from a waste liquor collected after coupling reaction in peptide syntheses with suppressing racemization of the amino acid derivatives.

Through extensive studies of various methods to suppress racemization, the present inventors found that racemization occurred in the process where the carboxyl group of the amino acid derivative which is activated for coupling reaction, i.e., the active ester was hydrolyzed to a free carboxyl group by an aqueous alkali treatment, even when a weak alkali was used, and that racemization was significantly suppressed when the hydrolysis of the active ester was carried out under the acidic conditions in the presence of a tertiary amine. The present inventors also found that racemization was almost completely suppressed, when large excess of 1-hydroxybenzotriazole (HOBt) or the like was added into the waste liquor immediately after the waste liquor was collected. The present inventors made further investigation based on these findings, and have developed the present invention.

Specifically, the present invention is mainly concerned with:

(1) A method for recovering an optically pure amino acid derivative from a waste liquor collected after a coupling reaction in peptide synthesis, comprising the steps of:

(a) adding into the waste liquor, in which an uncoupled amino acid derivative or an uncoupled small peptide fragment is contained, a compound selected from the group consisting of 1-hydroxybenzotriazole (HOBt), 1-hydroxy-7-azabenzotriazole (HOAt), 3-hydroxy-4-oxo-3,4-dihydro-1,2,3-benzotriazine (HOObt) and N-hydroxy-5-norbornen-2,3-dicarboxylic acid imide (HONB);

(b) concentrating the waste liquor obtained in step (a);

(c) treating a residue obtained in step (b) with an acidic buffer solution containing a tertiary amine; and (d) extracting and purifying the uncoupled amino acid derivative or the uncoupled small peptide fragment under acidic conditions;

(2) The method described in (1) above, wherein the compound in step (a) is added in an amount of 5 to 20 fold equivalents of the amount of the uncoupled amino acid derivative or the uncoupled small peptide fragment contained in the waste liquor;

(3) The method described in (1) above, wherein pH of the acidic buffer solution containing a tertiary amine is in the range of from 2 to 4; and (4) The method described in (1) above, wherein the tertiary amine is selected from the group consisting of triethylamine, trimethylamine and diisopropylethylamine.

DETAILED DESCRIPTION OF THE INVENTION

The present invention is described in more detail below.

The method of the present invention for recovering an optically pure amino acid derivative provides the possibility to reuse the recovered and regenerated acyl component, which can be achieved by suppressing racemization. Though it is known that the use of HOBt in coupling can suppress the racemization of the amino acid coupled, the suppression of racemization of recovered acyl components has been a problem which has not yet been solved by the conventional methods in recovering and regenerating of acyl components.

As a rule, the present method can be applicable to any amino acid derivatives and peptide fragments, regardless of the kinds of protecting groups therefor.

The solution used in the present invention, which contains an amino acid derivative, is a waste liquor collected after each coupling reaction of a preparative, or large scale peptide synthesis (hereinafter referred to as "the waste liquor"). The waste liquor normally contains an amino acid derivative, i.e., an uncoupled acyl component, in about 1 to 10 fold excess amount actually consumed in each coupling reaction. According to a study by the present inventors, if stored as is, the amino acid derivative contained in the waste liquor is racemized with time not only at room temperature but also at low temperatures such as −20° C. It is therefore preferable that the method of the present invention for recovering an optically pure amino acid derivative be carried out as soon as possible after a waste liquor is collected. In consideration of practical situation, however, the method of the present invention can be carried out within two days to a week after the collection of the waste liquor.

Although the waste liquor is normally a methylene chloride or dimethylformamide (DMF) solution, the present invention is applicable to any waste solution regardless of the type of solvent used.

The first feature of the present invention is in that one of HOBt, HOAt, HOObt and HONB (hereinafter simply referred to as HOBt, etc.) is added to the waste liquor collected. The amount of HOBt, etc. added is 5 to 20 fold excess amount to the acyl components dissolved in the waste liquor. HOBt, HOAt, HOObt and HONB used in this step may be commercial products (e.g., those produced by Calbiochem-Novabiochem AG, Perceptive-Biosearch, etc.).

Next, the solvent is removed by distillation from the waste liquor to which HOBt, etc. has been added. To minimize side reactions such as racemization, the solvent is normally distilled off under the reduced pressure at room temperature or lower, preferably at a temperature below 4° C. for a short period of time to give a gum. The resulting residue is extracted with an organic solvent capable of forming two layers with water, such as ethyl acetate.

The second feature of the present invention is to treat the extract thus obtained with a tertiary amine in an acidic buffer, thereby hydrolyzing the activated carboxyl group of the amino acid derivative to a free carboxyl group. In conventional methods, the hydrolysis of the activated carboxyl group is performed by treatment with a weak alkali, such as aqueous sodium bicarbonate, in an attempt to minimize racemization. In the conventional methods, although the use of a weak alkali suppresses racemization to some extent as compared with the case where a strong alkali is used, the optical purity of the recovered amino acid derivative is not highly enough to permit its reuse in which optical purity is required. In the method of the present invention in which the hydrolysis is carried out with a tertiary amine contained in an acidic buffer solution after the addition of an excess amount of HOBt, etc., the activated carboxyl group of the amino acid derivative is completely hydrolyzed to a free carboxyl group without impairing the optical purity of the amino acid derivative. That is, the racemization of the amino acid derivative is sufficiently suppressed during the regeneration and recovery process to allow the reuse of the recovered amino acid derivative for the synthesis of biologically active peptides.

Tertiary amines which can be used in the present invention include triethylamine, trimethylamine and diisopropylethylamine. These tertiary amines can be commercially available and can be used as received. The tertiary amine is normally dissolved in an acidic medium of pH 2 to 4 at a concentration of about 0.05 to 0.5M, and mixed with the previously obtained extract or gum with stirring to hydrolyze the active ester of the carboxyl group of the amino acid derivative.

Although there is no limitation in choosing the acidic buffer, phosphate buffers are preferred. When the pH value of the buffer exceeds 4, racemization tends to occur, while pH values of less than 2 increase the possibility of cleavage of acid-labile protecting groups of the side chains of amino acids.

Treatment temperature is normally 4° to 40° C., preferably 10° C. to room temperature. Treatment temperatures less than 0° C. slow the hydrolysis, and some of the activated carboxyl groups remain to be unhydrolyzed. Treatment temperatures exceeding 40° C. are likely to cause not only racemization but also other side reactions.

The resulting regenerated amino acid derivative with a free carboxyl group can be isolated by a conventional extraction/purification method. For example, the above-mentioned acid buffer solution containing an amino acid derivative is thoroughly shaken with an organic solvent capable of forming two layers with water, and then the mixture is kept standing to transfer the amino acid derivative to the organic solvent layer. The organic solvent layer is then thoroughly washed with water or saturated NaCl solution, sufficiently dried over anhydrous sodium sulfate, magnesium sulfate, or the like. Then, the organic solvent is distilled off under the reduced pressure, followed by the addition of petroleum ether, or the like, to solidify or crystalize the amino acid derivative. The resulting solid or crystal is filtered off, and, if necessary, recrystallized from an appropriate solvent in the reported manner. Also, according to necessity, a chromatographic method may be additionally used in the purification process.

The organic solvent used to extract the amino acid derivative from the acidic buffer is preferably a solvent having relatively high polarity capable of forming two layers with water, such as ethyl acetate, butyl acetate, methylene chloride or chloroform.

When the acyl component to be recovered is insoluble in organic solvent, the following procedures may be used: The recovered solution containing, for example, activated Fmoc-His(Trt)-OH is concentrated at room temperature, triturated with $NaHCO_3$ solution (pH 7.0), decanted and then acidified with citric acid to pH 3.0 to give a gum. This gum is again treated with saturated $NAHCO_3$ solution and citric acid. This procedure is repeated five times to give a solid, which is dissolved in methanol, precipitated with aqueous citric acid and filtered.

The crystallized or solidified amino acid derivative obtained by the method of the present invention has a high optical purity. As demonstrated in the Examples, even in the case of Fmoc-histidine which is the amino acid derivative most liable to racemization, the content of D-isomer is less than 1% for crude precipitate, and less than 0.1% after recrystallization. In the case of Fmoc-phenylalanine or Fmoc-tyrosine, the content of D-isomer is less than 0.5% for crude crystals, and less than 0.08% after recrystallization. In the case of other Fmoc-amino acids which are relatively stable against racemization, the content of D-isomer is less than 0.1% for crude precipitate, which is below the detectable level of DL analysis. The high level of optical purity achieved by the present method allows the reuse of the amino acid derivatives for syntheses of biologically active peptides. The recovery rates of these crystallized amino acid derivatives are in the range of from 50 to 90 weight %, depending on the kind of amino acid derivative to be recovered.

According to the method of the present invention, an amino acid derivative with high optical purity can be recovered from the waste liquor collected after a preparative scale of peptide syntheses. Therefore, an uncoupled amino acid derivative remaining in the waste liquor, which has conventionally been discarded, can be recovered and reused, thereby significantly reducing the production cost of the peptide synthesis and contributing to a saving of natural resources and environmental protection.

EXAMPLES

The present invention is hereinafter described in more detail by means of the following working examples, but is not limited by them.

Example 1

An optically pure amino acid derivative was regenerated and recovered according to the method of the present invention, using a waste liquor collected after a coupling reaction of peptide synthesis carried out by the method of Nokihara et al. [American Laboratories, 41–45, August (1984)] using a prototype semi-large scale continuous-flow peptide synthesizer. Specifically, the histidine derivative which is not stable to racemization was selected as the amino acid derivative to be recovered. After coupling using L-NαFmoc-trityl(Trt)histidine and benzotriazol-1-yl-oxy-tris(pyrrolidino)phosphonium hexafluorophosphate (PyBOP) in the presence of HOBt and N-methylmorpholine, a waste liquor was collected. From the waste liquor, uncoupled histidine derivative was recovered.

Incidentally, it should be noted that it is relatively difficult to recover a desired amino acid derivative from a waste liquor after a highly efficient coupling using a phosphonium compound such as PyBOP and BOP, because of the presence of hexamethylphosphotriamide and other byproducts.

Recovery of L-NαFmoc-trityl(Trt)histidine

The coupling reaction of L-NαFmoc-trityl(Trt)histidine onto polymer support (13.2 mM equivalent) was performed with the mixture of 32.7 g (52.8 mM) of histidine derivative, 27.5 g (52.8 mM) of PyBOP, 7.13 g (52.8 mM) of HoBt and 8.71 mL (79.2 mM) of N-methylmorpholine (NMM) in dimethylformamide (DMF). The waste liquor (2.17 L) was collected, which may contain at least 39.6 mM histidine derivative, and immediately combined with 53.5 g (396 mM) of HOBt and the liquid was stored at −20° C. After 2 days, the waste liquor was treated as follows:

The waste liquor was distilled to remove DMF using a rotary evaporator in a water bath at 25° C. under the reduced pressure. To the resulting residue, 1,000 ml of 0.05M triethylamine-phosphate buffer (pH 2.25) was added, and the resulting precipitate was filtered off, washed with water 5 times, and dried. The dried product was then dissolved in methanol and precipitated by the addition of water. After the precipitate was collected and dried, it was recrystallized from toluene to yield 17.2 g of L-NαFmoc-trityl(Trt) histidine. The recovery and optical purity were about 70% and 99.90% ee, respectively.

The recovered L-NαFmoc-trityl(Trt)histidine was identified by liquor secondary ion mass spectrometry (LSIMS) after it was confirmed to be a single component by thin-layer chromatography and reverse-phase HPLC.

Reverse-phase HPLC was carried out using a Syn-ProPep® column (trade name) RPC18 (4.6×150 mm), manufactured by Shimadzu Corporation, at a flow rate of 1.2 ml/min, and UV detection at 215 nm was employed. Elution was performed by the gradient method using 0.05M triethylamine-phosphate buffer (pH 2.25) as eluent A and acetonitrile as eluent B (A:B=1:3) for 30 minutes.

LSIMS was performed using a magnet sector type mass spectrometer manufactured by Kratos. Optical purity was determined using a Shimadzu CAT model DLAA-1 according to the method of Nokihara (Nokihara et al., Frontiers and Horizons in Amino Acid Research, pp. 391–395, 1992).

Example 2

Recovery of L-NαFmoc-t-butyltyrosine

As described in Example 1, ca. 1,000 mL of the waste liquor was collected after coupling. For this coupling, four fold excess amount, 15.2 g (33.1 mM), of L-NαFmoc-t-butyltyrosine was activated in the presence of 17.22 g (33.1 mM) of PyBOP, 4.47 g (33.1 mM) of HOBt, and 3.46 mL (49.7 mM) of NMM in DMF.

Immediately after the collection of the waste liquor, 44.7 g (331 mM) of HOBt was added to the waste liquor, and the resulting liquor was stored at −20° C. After 2 days, the waste liquor was treated as follows:

The waste liquor was distilled to remove DMF under the reduced pressure at 25° C. The residual oil was dissolved in 700 ml of ethyl acetate combined with 300 ml of 0.05M triethylamine-phosphate buffer (pH 2.25), and then the mixture was stirred for 5 minutes. The aqueous layer was recovered. This procedure was repeated for further 2 times, the organic layer was washed with saturated NaCl solution, dried over anhydrous sodium sulfate, and concentrated under the reduced pressure. Then, petroleum ether was added to give a precipitate, which was recrystallized from acetonitrile. The crystal was filtered off and dried to give 5.7 g of L-NαFmoc-t-butyltyrosine. The recovery rate and optical purity were about 50% and 99.90% ee, respectively.

The recovered L-NαFmoc-t-butyltyrosine was confirmed to be a single component by reverse-phase HPLC and thin layer chromatography and identified by liquid secondary ion mass spectrometry (LSIMS).

Reverse-phase HPLC was performed using a SynProPep column (trade name) RPC18 (4.6×150 mm), manufactured by Shimadzu Corporation, at a flow rate of 1.2 ml/min, and UV detection at 215 nm was employed. Elution was performed by the gradient method using 0.05M triethylamine-phosphate buffer (pH 2.25) as eluent A and acetonitrile as eluent B (A:B=1:3) for 30 minutes.

LSIMS was performed using a magnet sector type mass spectrometer manufactured by Kratos. Optical purity was determined using a Shimadzu CAT model DLAA-1 according to the method of Nokihara (Nokihara et al., Frontiers and Horizons in Amino Acid Research, pp. 391–395, 1992).

Example 3

Recovery of L-NαFmoc-phenylalanine

As described in Example 2, ca. 900 mL of the waste liquor was collected after coupling. For this coupling, four fold excess amount, 10.2 g (26.4 mM), of L-NαFmoc-phenylalanine was activated in the presence of 13.7 g (26.4 mM) of PyBOP, and 4.35 mL (39.6 mM) of NMM in DMF.

Immediately after the collection of the waste liquor, 26.7 g (264 mM) of HOBt was added to the waste liquor, and the resulting liquor was stored at −20° C. After 2 days, the waste liquor was treated as follows:

The waste liquor was distilled to remove DMF under the reduced pressure at 25° C. The residual oil was dissolved in 600 ml of ethyl acetate. Then 300 ml of 0.05M triethylamine-phosphate buffer (pH 2.25) was added to the mixture, stirred for 5 minutes. The aqueous layer was recovered. This procedure was repeated further 2 times, the organic layer was washed with saturated NaCl solution, dried over anhydrous sodium sulfate, and concentrated under the reduced pressure. Then, petroleum ether was added to give a precipitate, which was recrystallized from acetonitrile. The crystal was filtered off and dried to give 5.5 g of L-NαFmoc-phenylalanine. The recovery rate and optical purity were about 72% and 99.90% ee, respectively.

The recovered L-NαFmoc-phenylalanine was confirmed to be a single component by reverse-phase HPLC and thin layer chromatography and identified by liquid secondary ion mass spectrometry (LSIMS).

Reverse-phase HPLC was performed using a Syn-ProPep® column (trade name) RPC18 (4.6×150 mm), manufactured by Shimadzu Corporation, at a flow rate of 1.2 ml/min, and UV detection at 215 nm was employed. Elution was performed by the gradient method using 0.05M triethylamine-phosphate buffer (pH 2.25) as eluent A and acetonitrile as eluent B (A:B=1:3) for 30 minutes.

LSIMS was performed using a magnet sector type mass spectrometer manufactured by Kratos. Optical purity was determined using a Shimadzu CAT model DLAA-1 according to the method of Nokihara (Nokihara et al., Frontiers and Horizons in Amino Acid Research, pp. 391–395, 1992).

Example 4

Recovery of L-NαFmoc-trityl(Trt)histidine

As described in Example 1, ca. 600 mL of the waste liquor was collected after coupling. For this coupling, four fold excess amount, 8.2 g (13.2 mM), of L-NαFmoc-trityl(Trt) histidine was activated in the presence of 6.9 g (13.2 mM) of PyBOP, and 2.18 mL (19.8 mM) of NMM in DMF.

Immediately after the collection of the waste liquor, 13.5 g (99 mM) of HOAt was added to the waste liquor, and the resulting liquor was stored at −20° C. After 2 days, the waste liquor was treated as follows:

The waste liquor was distilled to remove DMF under the reduced pressure at 25° C. under the reduced pressure. To the resulting residue, 300 ml of 0.05M triethylamine-phosphate buffer (pH 2.25) was added, and the resulting precipitate was filtered off, washed with water 5 times, and dried. The dried product obtained was then dissolved in methanol and precipitated by the addition of water. After the precipitate was collected and dried, it was recrystallized from toluene to give 4.4 g of L-NαFmoc-trityl(Trt)histidine. The recovery rate and optical purity were about 72% and 99.93% ee, respectively.

The recovered L-NαFmoc-trityl(Trt)histidine was confirmed to be a single component by thin-layer chromatography and reverse-phase HPLC and identified by liquid secondary ion mass spectrometry (LSIMS).

Reverse-phase HPLC was carried out using a Syn-ProPep® column (trade name) RPC18 (4.6×150 mm), manufactured by Shimadzu Corporation, at a flow rate of 1.2 ml/min, and UV detection at 215 nm was employed. Elution was performed by the gradient method using 0.05M triethylamine-phosphate buffer (pH 2.25) as eluent A and acetonitrile as eluent B (A:B=1:3) for 30 minutes.

LSIMS was performed using a magnet sector type mass spectrometer manufactured by Kratos. Optical purity was determined using a Shimadzu CAT model DLAA-1 according to the method of Nokihara (Nokihara et al., Frontiers and Horizons in Amino Acid Research, pp. 391–395, 1992).

Example 5

Recovery of L-NαFmoc-trityl(Trt)histidine

As described in Example 1, ca. 650 mL of the waste liquor was collected after coupling. For this coupling, four fold excess amount, 6.20 g (10.0 mM), of L-NαFmoc-trityl(Trt) histidine was activated in the presence of 5.20 g (10.0 mM) of PyBOP, 13.5 g (10.0 mM) of HOBt, and 1.65 mL (15.0 mM) of NMM in DMF.

Immediately after the collection of the waste liquor, 12.1 g (80 mM) of HOBt was added to the waste liquor, and the resulting liquor was stored at −20° C. After 2 days, the waste liquor was treated as follows:

The waste liquor was distilled to remove DMF using a rotary evaporator in a water bath at 25° C. under the reduced pressure. To the resulting residue, 400 ml of 0.05M triethylamine-phosphate buffer (pH 2.25) was added, and the resulting precipitate was filtered off, washed with water 5 times, and dried. The dried product was then dissolved in methanol and precipitated by the addition of water. After the precipitate was collected and dried, it was recrystallized from toluene to yield 3.3 g of L-NαFmoc-trityl(Trt) histidine. The recovery and optical purity were about 71% and 99.92% ee, respectively.

The recovered L-NαFmoc-trityl(Trt)histidine was identified by liquor secondary ion mass spectrometry (LSIMS) after it was confirmed to be a single component by thin-layer chromatography and reverse-phase HPLC.

Reverse-phase HPLC was carried out using a Syn-ProPep® column (trade name) RPC18 (4.6×150 mm), manufactured by Shimadzu Corporation, at a flow rate of 1.2 ml/min, and UV detection at 215 nm was employed. Elution was performed by the gradient method using 0.05M triethylamine-phosphate buffer (pH 2.25) as eluent A and acetonitrile as eluent B (A:B=1:3) for 30 minutes.

LSIMS was performed using a magnet sector type mass spectrometer manufactured by Kratos. Optical purity was determined using a Shimadzu CAT model DLAA-1 according to the method of Nokihara (Nokihara et al., Frontiers and Horizons in Amino Acid Research, pp. 391–395, 1992).

Example 6

Recovery of L-NαFmoc-trityl(Trt)histidine

As described in Example 1, ca. 200 mL of the waste liquor was collected after coupling. For this coupling, four fold excess amount, 3.3 g (5.28 mM), of L-NαFmoc-trityl(Trt) histidine was activated in the presence of 2.75 g (5.28 mM) of PyBOP, 0.71 g (5.28 mM) of HOBt, and 0.87 mL (7.92 mM) of NMM in DMF. Immediately after the collection of the waste liquor, the waste liquor was combined with 9.5 g (52.8 mM) of HONB and stored at −20° C. After 2 days, the waste liquor was treated as follows:

The waste liquor was distilled to remove DMF using a rotary evaporator in a water bath at 25° C. under the reduced pressure. To the resulting residue, 200 ml of 0.05M triethylamine-phosphate buffer (pH 2.25) was added, and the resulting precipitate was filtered off, washed with water 5 times, and dried. The dried product was then dissolved in methanol and precipitated by the addition of water. After the precipitate was collected and dried, it was recrystallized from toluene to yield 1.8 g of L-NαFmoc-trityl(Trt) histidine. The recovery and optical purity were about 73% and 99.92% ee, respectively.

The recovered L-NαFmoc-trityl(Trt)histidine was identified by liquor secondary ion mass spectrometry (LSIMS) after it was confirmed to be a single component by thin-layer chromatography and reverse-phase HPLC.

Reverse-phase HPLC was carried out using a Syn-ProPep® column (trade name) RPC18 (4.6×150 mm), manufactured by Shimadzu Corporation, at a flow rate of 1.2 ml/min, and UV detection at 215 nm was employed. Elution was performed by the gradient method using 0.05M triethylamine-phosphate buffer (pH 2.25) as eluent A and acetonitrile as eluent B (A:B=1:3) for 30 minutes.

LSIMS was performed using a magnet sector type mass spectrometer manufactured by Kratos. Optical purity was determined using a Shimadzu CAT model DLAA-1 according to the method of Nokihara (Nokihara et al., Frontiers and Horizons in Amino Acid Research, pp. 391–395, 1992).

Example 7

Recovery of L-Nα-tert-butyloxycarbonyl(Boc)-phenylalanine

This example describes L-Nα-tert-butyloxycarbonyl (Boc)-phenylalanine regeneration without significant racemization to mimic the recovery after coupling in assembly of peptides.

L-Nα-tert-butyloxycarbonyl(Boc)-phenylalanine (2.65 g, 10.0 mM) was preactivated in the presence of PyBOP (4.66 g, 10.0 mM), HOBt (13.5 g, 10.0 mM) and NMM(1.65 mL, 15.0 mM) in 50 mL of DMF. After 30 minute stirring, the mixture was diluted to 250 mL with DMF and combined with HOBt (13.5 g, 100 mM). The mixture was then concentrated under the reduced pressure as described in Examples 1 and 2. The residual oil was dissolved in ethyl acetate (500 mL), washed 3 times with 0.05M triethylamine phosphate buffer (pH 2.25) followed by saturated NaCl solution. The organic layer was dried over $Na_2SO_4$ and then concentrated. The residue was solidified by the addition of petroleum ether (PE). Reprecipitation was performed from ethylacetate and PE to give 1.4 g (75%) of L-Nα-tert-butyloxycarbonyl(Boc)-phenylalanine. Optical purity was 99.92% ee.

The recovered L-NαBoc-phenylalanine was confirmed to be a single component by reverse-phase HPLC and thin layer chromatography and identified by liquid secondary ion mass spectrometry (LSIMS).

Reverse-phase HPLC was performed using a Syn-ProPep® column (trade name) RPC18 (4.6×150 mm), manufactured by Shimadzu Corporation, at a flow rate of 1.2 ml/min, and UV detection at 215 nm was employed. Elution was performed by the gradient method using 0.05M triethylamine-phosphate buffer (pH 2.25) as eluent A and acetonitrile as eluent B.

LSIMS was performed using a magnetic field type mass spectrometric manufactured by Kratos. Optical purity was determined using a Shimadzu CAT model DLAA-1 according to the method of Nokihara (Nokihara et al., Frontiers and Horizons in Amino Acid Research, pp. 391–395, 1992).

The present invention being thus described, it will be obvious that the same may be varied in many ways. Such variations are not to be regarded as a departure from the spirit and scope of the invention, and all such modifications as would be obvious to one skilled n the art are intended to be included within the scope of the following claims.

What is claimed is:

1. A method for recovering amino acid or peptide derivatives having at least one chiral carbon atom with an activated carboxyl group as an active ester from a liquor, comprising the steps of:

(a) adding into the liquor a compound selected from the group consisting of 1-hydroxybenzotriazole (HOBt), 1-hydroxy-7-azabenzotriazole (HOAt), 3-hydroxy-4-oxo-3,4-dihydro-1,2,3-benzotriazine (HOObt) and N-hydroxy-5-norbornen-2,3-dicarboxylic acid imide (HONB);

(b) concentrating the liquor obtained in step (a);

(c) treating concentrated liquor obtained in step (b) with an acidic buffer solution containing a tertiary amine wherein the active ester is hydrolyzed to a free carboxyl group and retains its optical configuration without racemization; and (d) extracting and purifying the amino acid or the peptide derivatives under acidic conditions.

2. The method according to claim 1, wherein the compound in step (a) is added in an amount of 5 to 20 times the amount of the amino acid or peptide derivatives contained in the liquor.

3. The method according to claim 1, wherein pH of the acidic buffer solution containing a tertiary amine is in the range of from 2 to 4.

4. The method according to claim 1, wherein the tertiary amine is selected from the group consisting of triethylamine, trimethylamine and diisopropylethylamine.

5. The method according to claim 1, wherein said method occurs at a temperature of 4° to 40° C.

6. The method according to claim 1, wherein L-NαFmoc-trityl(Trt)histidine is recovered.

7. The method according to claim 1, wherein L-NαFmoc-t-butyltyrosine is recovered.

8. The method according to claim 1, wherein L-NαFmoc-phenylalanine is recovered.

* * * * *